US009988335B2

(12) United States Patent
Schütze et al.

(10) Patent No.: US 9,988,335 B2
(45) Date of Patent: Jun. 5, 2018

(54) METHOD AND APPARATUS FOR CONCENTRATION AND CRYSTALLIZATION OF FERMENTABLE CARBOXYLIC ACIDS

(71) Applicants: ThyssenKrupp Industrial Solutions AG, Essen (DE); ThyssenKrupp AG, Essen (DE)

(72) Inventors: Joachim Schütze, Torgau (DE); Gerd Braun, Overath (DE)

(73) Assignees: THYSSENKRUPP INDUSTRIAL SOLUTIONS AG, Essen (DE); THYSSENKRUPP AG, Essen (DE)

( * ) Notice: Subject to any disclaimer, the term of this patent is extended or adjusted under 35 U.S.C. 154(b) by 0 days. days.

(21) Appl. No.: 15/326,139

(22) PCT Filed: Jul. 3, 2015

(86) PCT No.: PCT/EP2015/065239
§ 371 (c)(1),
(2) Date: Jan. 13, 2017

(87) PCT Pub. No.: WO2016/008745
PCT Pub. Date: Jan. 21, 2016

(65) Prior Publication Data
US 2017/0217871 A1  Aug. 3, 2017

(30) Foreign Application Priority Data

Jul. 14, 2014 (DE) .......................... 10 2014 213 637

(51) Int. Cl.
| | |
|---|---|
| *C07C 51/43* | (2006.01) |
| *B01D 15/36* | (2006.01) |
| *B01D 61/36* | (2006.01) |
| *B01D 15/42* | (2006.01) |
| *B01D 9/00* | (2006.01) |
| *B01D 61/02* | (2006.01) |

(52) U.S. Cl.
CPC ............ *C07C 51/43* (2013.01); *B01D 9/0013* (2013.01); *B01D 9/0059* (2013.01); *B01D 15/361* (2013.01); *B01D 15/426* (2013.01); *B01D 61/022* (2013.01); *B01D 61/364* (2013.01); *B01D 2311/2623* (2013.01); *B01D 2311/2642* (2013.01); *B01D 2317/025* (2013.01)

(58) Field of Classification Search
CPC .... C07C 51/43; B01D 9/0013; B01D 9/0059; B01D 15/361; B01D 15/426; B01D 61/022; B01D 61/364; B01D 2311/2623; B01D 2311/2642; B01D 2317/025
USPC ....................................... 548/339.1
See application file for complete search history.

(56) References Cited

U.S. PATENT DOCUMENTS

| | | |
|---|---|---|
| 5,090,965 A | 2/1992 | Kehm et al. |
| 5,352,825 A | 10/1994 | Felman et al. |
| 6,630,603 B1 | 10/2003 | Van Breugel et al. |
| 2004/0060322 A1 | 4/2004 | Witkamp et al. |
| 2013/0096343 A1 | 4/2013 | Tietz et al. |
| 2013/0116471 A1 | 5/2013 | Yan et al. |
| 2015/0344397 A1 | 12/2015 | Kleiber et al. |

FOREIGN PATENT DOCUMENTS

| | | |
|---|---|---|
| DE | 19939630 A1 | 3/2001 |
| WO | 2013/042760 A1 | 3/2013 |
| WO | 2014/106532 A2 | 7/2014 |

OTHER PUBLICATIONS

International Search Report for PCT/EP2015/065239 (dated Oct. 1, 2015).
English Language Abstract for DE 19939630 A1, 2001.

*Primary Examiner* — Kristin A Vajda
(74) *Attorney, Agent, or Firm* — thyssenkrupp North America, Inc.

(57) ABSTRACT

A method for concentrating and crystallizing fermentable carboxylic acids, salts, and mixtures thereof may involve the use of carboxylic acids that have a defined temperature dependence of the solubility and of the osmotic pressure. The carboxylic acids may be concentrated by a membrane method and subsequently crystallized out by a cooling crystallization and isolated. In some examples, the membrane method may involve nanofiltration, reverse osmosis, and/or membrane distillation for separation into a concentrate and a permeate. Similarly, an apparatus for implementing such methods may include a nanofiltration, reverse osmosis, and/or membrane distillation unit for concentrating the carboxylic acid, and at least one cooling crystallization unit for crystallizing the carboxylic acid.

21 Claims, 3 Drawing Sheets

METHOD AND APPARATUS FOR CONCENTRATION AND CRYSTALLIZATION OF FERMENTABLE CARBOXYLIC ACIDS

CROSS REFERENCE TO RELATED APPLICATIONS

This application is a U.S. National Stage Entry of International Patent Application Serial Number PCT/EP2015/065239, filed Jul. 3, 2015, which claims priority to German Patent Application No. DE 102014213637.7 filed Jul. 14, 2014, the entire contents of both of which are incorporated herein by reference.

FIELD

The present disclosure generally relates to apparatuses and methods for concentrating and crystallizing fermentable carboxylic acids, salts, and mixtures thereof.

BACKGROUND

Critical to the industrial utilization of organic acids which are generated by fermentation of carbohydrate-containing substrates by various microorganisms, or which come from synthesis solutions, are the economics and efficiency of the purification, concentration and the crystallization.

WO 2011/160760 A1 discloses a method for removing, recovering and purifying dicarboxylic acids. It describes removal of the biomass from the fermentation broth in two consecutive filtration steps. The dicarboxylic acid solution is subsequently removed from the biomass-free fermentation broth by means of Simulated Moving Bed (SMB) chromatography. After fine purification through a membrane system, activated carbon filter and/or cation exchanger and/or anion exchanger, the purified dicarboxylic acid solution undergoes a multistage evaporative operation for concentration, followed by an evaporative crystallization. In the crystallization, there is slow cooling of the concentrated dicarboxylic acid in steps of 3° C. to 8° C./min, preferably 3° C. to 5° C./min, and, for obtaining high-purity dicarboxylic acid, in steps of 1° C. to 5° C./h. For the recovery of high-purity crystals, the evaporative concentration operation and the crystallization are repeated a number of times. For this purpose the crystals are dissolved in demineralized water and/or vapor condensate. The residual crystallization solution arising after crystallization, through separation of the crystals, and referred to hereinafter as mother liquor, is returned before the evaporative concentration. This method can be implemented for dicarboxylic acids selected from the group of fumaric acid, maleic acid, adipic acid, itaconic acid, benzoic acid and others, especially succinic acid.

DE 38 27 455 C2 describes a method for separation. In the case of this method, a single-stage or multistage fractional cooling crystallization is utilized, and the mixture, which fills the crystallizer completely, is set into vibration by means of forced oscillations in the course of solidification. After the end of the solidification, the remaining mixture is removed and the crystal layer is melted off in a plurality of temperature stages, a melt of identical composition being introduced into the crystallizer for the melting-off operation. The fractions recovered accordingly are collected individually. The apparatus for this method consists of a crystallizer with heat exchanger and an associated temperature circuit. The heat exchanger is preceded by a compensating vessel which has a separate conditioning circuit, and a liquid-phase vessel is connected at the bottom of the heat exchanger. Beneath the liquid phase there is an oscillating device which sets the mixture in the crystallizer into turbulent vibrations during solidification.

DE 600 14 047 T2 describes a method in which a dilute lactic acid concentrate is crystallized by direct cooling in one or more melt crystallizers, or is crystallized by means of one or more cooling crystallizers and/or evaporative crystallizers and/or one or more adiabatic crystallizers. In this case, seed crystals are used for the method of crystallization.

DE 600 28 806 T2 presents a method wherein selected salts, such as potassium, magnesium and ammonium salts, nitrates, phosphates, sulfates and organic salts, are obtained from an aqueous solution, such as a liquid agricultural or fermentation byproduct or a derivative thereof, a waste stream from an acid-catalyzed chemical process, an aqueous solution from gas scrubbing of off-gases from an agricultural stall for the keeping of cattle, or an aqueous solution from the processing of cattle manure. These salts are crystallized by freeze crystallization, with ice and crystallized material being separated from one another by exploiting their density properties and/or their difference in particle size.

DE 10 2012 105 128 A1 discloses a method by means of cooling crystallization for purifying or processing long-chain dicarboxylic acids or one of their salts. In this case the crude material is first acidified to a pH of 1 to 2.5 at a temperature from 60° C. to 100° C., and the precipitating crude product is collected, and dissolved by addition of an alkaline solution (5M NaOH), with a pH of 1 to 2.5 being retained. Subsequently the dicarboxylic acid is heated at 80° C. for an hour and melted and insoluble material is removed by filtering, the filter medium consisting one kind of several kinds of gauze, nylon membrane, ceramic foil, metal foil and glass fiber membrane. The dicarboxylic acid is decolorized using 0.2 wt % of activated carbon or 0.5 wt % of silica and is thereafter acidified again to a pH of 1 to 2.5. After centrifugation, the resulting precipitate of the dicarboxylic acid is collected and is washed one to ten times with water until neutral (pH 6.5 to 7) at a temperature of 85° C. This is followed by heating at 60° C. to 100° C., filtration, further washing and subsequent drying, producing a filtercake of the dicarboxylic acid, which is in turn suspended under high pressure in water and heated to >100° C., the temperature being maintained for 20 minutes above the melting point. Subsequently the temperature is slowly lowered to room temperature at 10° C. to 15° C./h, followed by further filtration of the dicarboxylic acid, in order to thus obtain the dicarboxylic acid crystals. In the method, alternatively, it is possible to omit the first heating and melting of the dicarboxylic acid, which takes place at 80° C. for 1 hour, and/or to omit the first acidification to a pH of 1 to 2.5.

A disadvantage of all of these methods is that the practical implementation of the methods entails considerable technical and energy expenditure and complexity.

DETAILED DESCRIPTION

Figure 1:
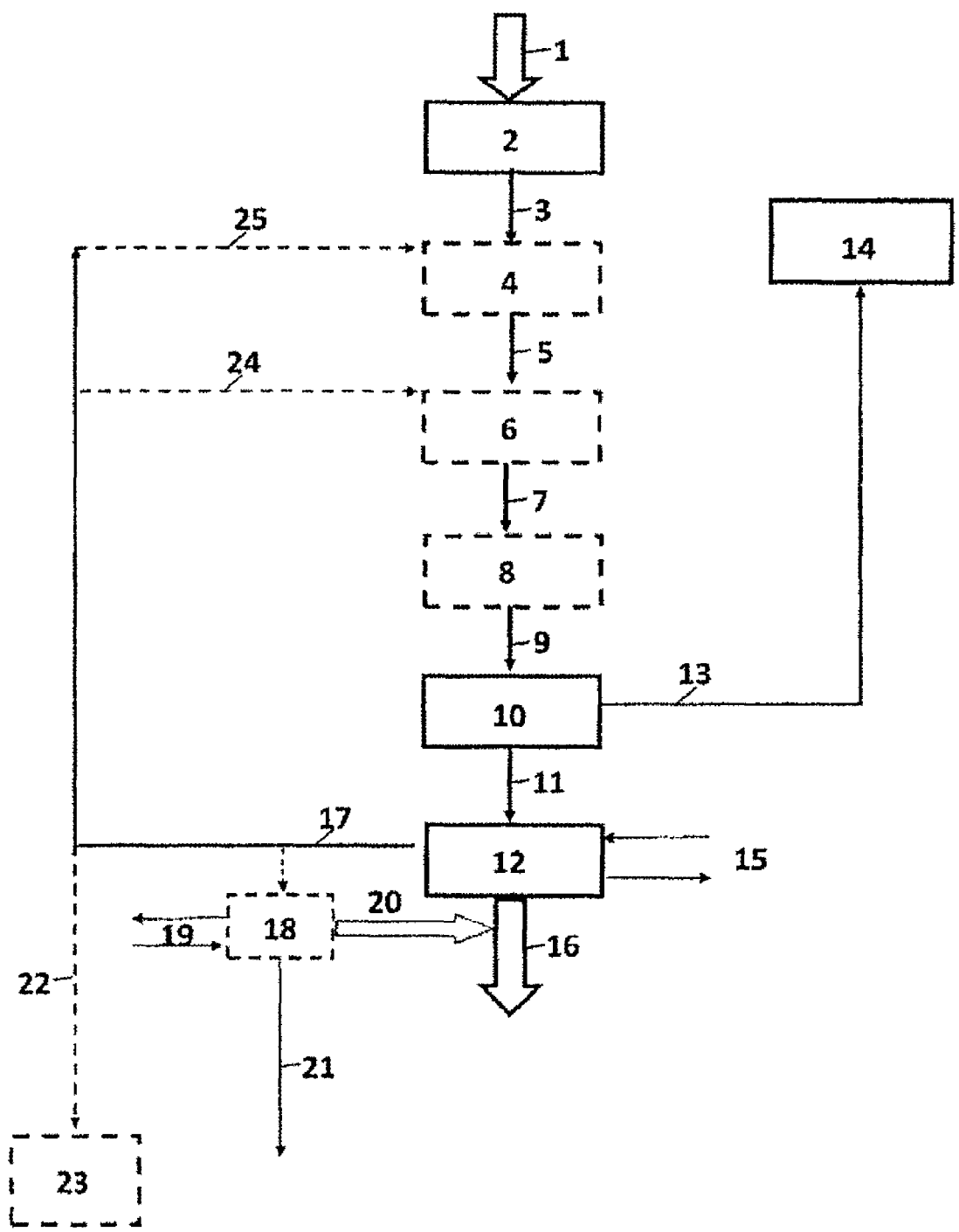
FIG. 1 is a flow diagram of an example method involving reverse osmosis.

Although certain example methods and apparatus have been described herein, the scope of coverage of this patent is not limited thereto. On the contrary, this patent covers all methods, apparatus, and articles of manufacture fairly falling within the scope of the appended claims either literally or under the doctrine of equivalents. Moreover, those having ordinary skill in the art will understand that reciting 'a' element or 'an' element in the appended claims does not restrict those claims to articles, apparatuses, systems, methods, or the like having only one of that element, even where other elements in the same claim or different claims are preceded by "at least one" or similar language. Similarly, it should be understood that the steps of any method claims need not necessarily be performed in the order in which they are recited, unless so required by the context of the claims. In addition, all references to one skilled in the art shall be understood to refer to one having ordinary skill in the art.

The present disclosure generally concerns methods for concentrating and crystallizing fermentable carboxylic acids, salts, and mixtures thereof. In some examples, carboxylic acids may be used that have a defined temperature dependence of the solubility and of the osmotic pressure, and may be subsequently concentrated by a membrane method and subsequently crystallized out by a cooling crystallization and isolated. The present disclosure also generally concerns apparatuses for implementing such methods, which apparatuses may include a nanofiltration, reverse osmosis, and/or membrane distillation unit for concentrating the carboxylic acid; and at least one cooling crystallization unit for crystallizing the carboxylic acid. To that end, one example object of the present disclosure is to provide an energetically-favorable overall process for the concentration and crystallization of fermentable carboxylic acids, which process avoids the above-described disadvantages of the prior art methods.

Provided in accordance with the invention is a method for concentrating and crystallizing carboxylic acids, salts and mixtures thereof, obtained by fermentation or from synthesis solution, wherein a) a processed fermentation broth or an aqueous solution of at least one carboxylic acid is provided, the at least one carboxylic acid being selected according to the following criteria:

the carboxylic acid possesses a molar mass in the range from 90 to 210 g/mol, the carboxylic acid possesses a solubility in water (at 20° C.) of 4 g/l to 100 g/l, the carboxylic acid possesses a relative increase in solubility in the temperature range from 20 to 80° C. of at least 2%/° C., relative to the solubility at 20° C., a concentrated solution of the carboxylic acid possesses an osmotic pressure in the temperature range from 20 to 80° C. in the range from 10 to 85 bar, preferably 30 to 80 bar, b) the carboxylic acid is concentrated in the solution by means of a membrane method, c) the concentrated solution of the carboxylic acid, subsequent to the membrane method, is subjected to a cooling crystallization, and d) the crystals of the carboxylic acid are isolated.

In the context of the present invention, carboxylic acids are frequently referred to, for reasons of simplification. This reference, however, is not only to the carboxylic acids but also to their salts and also mixtures thereof.

The costly and inconvenient evaporative concentration method known from the prior art for concentrating the carboxylic acids to be crystallized is replaced in accordance with the invention by a concentration by membrane methods, and the crystallization is carried out by means of a cooling crystallization, and so operates without refrigeration processes.

A particular advantage of the invention is that by virtue of the procedure used, it becomes possible to bring about controlled supersaturation in the cooling crystallizer under ambient conditions and, accordingly, to produce defined particle size distributions, thus allowing large crystals to be produced as a result of the easily controllable supersaturation, these crystals being able to grow slowly and hence avoiding incorporation of impurities into the crystal system, thereby making it possible to do without an additional purification step. The crystals have a particle size in the range from 0.1 to 3 mm, preferably from 0.2 to 1.5 mm. The particle size here is determined by means of sieve analysis in accordance with DIN 66165.

In one preferred embodiment of the present invention, the concentration in step b) takes place by a factor of 1 to 5, more particularly of 2 to 3.5, up to immediately before attainment of the solubility limit of the at least one carboxylic acid. Thus, for example, a carboxylic acid-containing solution can be concentrated from a carboxylic acid content of 5 wt % to a solution having a carboxylic acid content of 15 to 20 wt %.

As far as the temperature range for the concentration is concerned, it is set, in accordance with the dissolved component and its solubility behavior, in the range from preferably 30° C. to 90° C., the concentration being preferably carried out such as to attain in the concentrate a degree of concentration of approximately $\alpha=0.9 \ c(T)/C_{max}(T)$, so that the concentration in the concentrate is approximately 90% of the maximum possible solubility at this temperature.

The degree of concentration is preferably selected such that supersaturation of the solution and the therewith incipient crystallization take place on cooling to 10° C. to 40° C., more preferably from 25° C. to 30° C. Especially preferred in this context are temperatures of about 25° C., since this is easy to realize by means of cooling water.

The membrane method used in accordance with the invention for the concentration is preferably a reverse osmosis and/or nanofiltration and/or a membrane distillation, it also being possible to use any desired combinations of these three methods. The combination of these methods also allows solutions having an osmotic pressure of more than 40 bar to be concentrated.

For the embodiments of the invention in which a reverse osmosis is carried out as membrane method for the concentration, this reverse osmosis may be carried out in either one-stage form or else two-stage or multistage form. Preferred here is the two-stage implementation of the reverse osmosis, with the permeate of the first reverse osmosis stage preferably being supplied to the second reverse osmosis stage, and the permeate of the second reverse osmosis stage preferably being supplied again to the method elsewhere, especially for preparing the nutrient solutions for the fermentation. The concentrate of the first reverse osmosis stage is subsequently supplied to the cooling crystallization of the invention.

In another preferred embodiment of the method of the invention, the membrane method used for concentration comprises a membrane distillation, with the distillate of the membrane distillation preferably being supplied again to the method elsewhere. The distillate may be supplied, for example, as eluent for subsequent chromatographic purification steps, in the SMB chromatography, for example. The membrane distillation is carried out here preferably at temperatures immediately below the solubility limit of the carboxylic acid used, preferably in the range from 40° C. to 80° C. Where succinic acid is the carboxylic acid concentrated in the method of the invention, the concentration takes place preferably at temperatures in the range from 40° C. to 60° C.

The use of a membrane method for concentrating the organic solutions also represents a purification step, since ingredients with a molecular mass lower than that of the target compounds and salts to be crystallized out are able to pass through the membrane (especially in the case of the method of nanofiltration) and hence are unable to get into the crystallizate.

In the case of an additional adsorption step (for example, activated carbon), retained contaminants are present at elevated concentration, thereby allowing them to be removed more effectively from the solution—that is, a higher loading of the adsorbent is enabled.

In order to obtain the organic solutions in crystalline form, they are cooled and crystallized using a cooling crystallizer, preferably a contact crystallizer.

In this cooling crystallization, the crystals are precipitated in the mother liquor, and the mother liquor separated from the crystals is preferably returned into the method. This may be done, for example, by drawing off and heating the mother liquor and then returning it to the feed reservoir for the reverse osmosis, with the mother liquor drawn off being recycled from the recycle stream
- into an upstream process stage, preferably before the nanofiltration, or
- being subsequently supplied to a cooling crystallization in a small contact crystallizer with cold water or cooling brine as cooling medium, or
- the depleted mother liquor being processed further.

In one embodiment of the invention, the depleted mother liquor is processed further for esterification reactions.

In order to obtain the organic carboxylic acids in crystalline form, they are cooled and crystallized with a cooling crystallizer, and
- on cooling, organic acid precipitates from the concentrated solution in accordance with the solubility curve and the selected temperature for the reverse osmosis, with the product crystallization in the cooling crystallizer being carried out at 70% to 95% on the solubility curve of the solution, preferably at 90% of the solubility curve,
- on cooling, a temperature of 30° C. is preferably set in the crystallizer in the case of a combination of reverse osmosis and cooling crystallizer,
- the crystal suspension drawn off from the contact crystallizer is subjected to a further, conventional crystal workup.

In view of the coupling of the membrane method with the cooling crystallization, it is preferred if the concentrate from the membrane method is subjected to regenerative heat exchange in a heat exchanger and the heat exchange takes place with a mother liquor drawn off from the cooling crystallization, the concentrate being preferably cooled to a temperature of 30° C. to 40° C. and subsequently supplied to the cooling crystallization. Here, preferably, the mother liquor heated in the heat exchanger is returned to the processed fermentation solution in a), the mother liquor, before being fed in, being preferably purified by nanofiltration and/or ion exchange.

In relation to the cooling crystallization carried out in accordance with the invention, preferably, the cooling crystallization is carried out in two-stage form, the first stage of the cooling crystallization comprising cooling with the mother liquor drawn off from the cooling crystallizer, and the second stage of the cooling crystallization comprising cooling with externally supplied cooling water or cooling brine.

A further embodiment of the invention provides for at least one of the following steps to be carried out in the processing of the fermentation broth:
  i. removal of the biomass from the fermentation broth by a first step of centrifugation, separation, precoat filtration and/or microfiltration and also a second step of ultrafiltration,
  ii. optionally, polishing of the biomass-free fermentation broth by a purification method selected from the group consisting of nanofiltration, cation exchange, anion exchange, activated carbon purification, and combinations thereof, more particularly
    combination of nanofiltration with cation exchange, anion exchange, and activated carbon purification,
    combination of nanofiltration with cation exchange and anion exchange,
    combination of nanofiltration with cation exchange,
    combination of nanofiltration with cation exchange and activated carbon purification,
    combination of nanofiltration with activated carbon purification,
  iii. acidification of the fermentation broth remaining from A) or B) with sulfuric acid, preferably to a pH of 1.8 to 3.0, more preferably of 2.0 to 2.5,
  iv. implementation of an SMB chromatography, more particularly with an anion or cation exchanger resin, with the solution resulting from C).

In one refinement of the invention, for the processing and crystallization of organic carboxylic acids from fermentation broths which are taken from a fermenter, the biomass is separated from the solution and the solution is purified, the removal of the biomass being accomplished in a first step, without lowering the pH by addition of acid and without thermal deactivation by precoat filtration and/or microfiltration, and also by a single-stage or multistage ultrafiltration with membranes, the cutoff limit of the ultrafiltration membranes being ≤10 kDa.

In one refinement of the invention, for further purification of the solution, the biomass-free fermentation broth is acidified with concentrated sulfuric acid to a pH of 2.2 to 2.4, then subjected to a Simulated Moving Bed (SMB) chromatography and, after acidification, the salt of the carboxylic acid present in the purified fermenting solution is converted into solution, the temperature of the acidified ultrafiltration permeate being maintained in a range between 30° C. and 60° C. and preferably in a range between 30° C. and 40° C.

In one refinement of the invention, the time between removal of the fermentation broth from the fermenter and the filtration in a precoat filtration and/or microfiltration is not more than 2 h, preferably less than 1 h, the filtrate draw being adjusted such that the biomass concentration in the filtrate obtained is not greater than 1 g/l.

In one refinement of the invention, the ultrafiltration permeate of a Simulated Moving Bed (SMB) chromatography is separated into an extract containing 99% of the organic solutions (amount of ≤1 g/l) and a raffinate containing inorganic salts, among other constituents, with the organic solution binding to a stationary SMB phase composed of a cation exchanger and/or an anion exchanger.

In one refinement of the invention, the separation of the extract containing the organic solutions from the raffinate in the SMB is adjusted such that the efficiency of the recovery of the organic solutions from the ultrafiltration permeate is ≥95%.

In one refinement of the invention, the biomass-free fermentation broth or the synthesis solution is subjected to a polishing operation, where, depending on the aqueous solution to be treated and the quality required in the end product (in respect of the purity of the crystals), the polishing steps (nanofiltration, ion exchanger and activated carbon column) are combined differently.

In one refinement of the invention, in order to obtain a high purity of ≥99%, a nanofiltration is combined with a cation exchange, an anion exchange and an activated carbon purification.

In one refinement of the invention, in order to obtain a high purity of ≥99%, a nanofiltration is combined with a cation exchange and an anion exchange.

In one refinement of the invention, in order to obtain a technical grade quality with a purity of at least 90%, a nanofiltration is combined with a cation exchange.

In one refinement of the invention, in order to obtain a technical grade quality with a purity of at least 90%, a cation exchange is combined with an anion exchange and an activated carbon purification.

In one refinement of the invention, in order to obtain an inferior technical grade quality with a purity of ≤90%, a cation exchange is combined with an activated carbon purification.

In one refinement of the invention, in order to obtain a technical grade quality with a purity of at least 90%, a nanofiltration is carried out.

In one refinement of the invention, when using pure starting materials, as in the processing of synthesis products, there is no purification by means of the stated polishing steps.

In one refinement of the invention, the nanofiltration takes place using membranes which possess a cutoff limit of 100 Da to 400 Da, preferably 200 Da.

The carboxylic acids preferably have a molar mass of 110 g/mol to 150 g/mol and/or a solubility in water (at 20° C.) of 15 g/l to 90 g/l. The carboxylic acids here are preferably selected from the group consisting of fumaric acid, succinic acid, adipic acid, itaconic acid, threonine, methionine, aspartic acid, glutaric acid, asparagine, glutamine, histidine, isoleucine, phenylalanine, tryptophan, tyrosine, and valine, salts thereof, and mixtures thereof. Particularly preferred are succinic acid, adipic acid, itaconic acid, threonine and methionine.

Likewise provided in accordance with the invention is an apparatus for concentrating and crystallizing carboxylic acids, salts and mixtures thereof obtained by fermentation or from synthesis solution, said apparatus comprising the following units:

A) at least one nanofiltration, reverse osmosis and/or membrane distillation unit for separating the processed fermentation broth originating from a fermenter into at least one concentrate stream and at least one permeate stream, B) at least one single-stage or multistage cooling crystallization unit for crystallizing the carboxylic acid out of the solution representing it.

The units A) and B) here are connected via at least one line for transferring the concentrate stream into the unit B), and also the unit A) has at least one diverting line for recycling the at least one permeate stream into the process, and the unit B) has at least one recycle line for the mother liquor as coolant for the cooling crystallization unit.

In one preferred embodiment of the apparatus of the invention, the unit A) consists of a two-stage reverse osmosis unit, the first stage being connected to the second stage of the reverse osmosis unit via a permeate stream line for transferring the permeate stream from the first stage into the second stage.

The unit B) of the apparatus of the invention may consist preferably of a two-stage cooling crystallization unit with separate coolant system, the second stage being connected to the first stage via at least one recycle line for the mother liquor with the coolant system of the first stage, and the coolant system of the second stage having a separate feed line for a coolant.

With further preference, the line for transferring the concentrate stream from unit A) to unit B) is interrupted by at least one heat exchanger which, for the concentrate stream, has a feed line from the unit A) and a diverting line to the unit B), and, for the mother liquor, has a feed line from the unit B) and a diverting line to the processed fermentation broth, thereby enabling regenerative heat exchange between concentrate stream and mother liquor stream.

The cooling crystallization unit consists, in one preferred embodiment, of a contact crystallizer.

The apparatus of the invention further preferably has the following additional units for processing the fermentation broth:

I. removal unit for removing the biomass from the fermentation broth, selected from the group consisting of centrifuge, separator, precoat filtration unit, microfiltration unit, ultrafiltration unit, and combinations thereof, II. optionally a purification unit for polishing the biomass-free fermentation broth, selected from the group consisting of nanofiltration unit, cation exchanger, anion exchanger, activated carbon purification unit, and combinations thereof, III. reactor for acidifying the fermentation broth remaining from A) or B) with sulfuric acid, preferably to a pH of 1.8 to 3.0, more preferably of 2.0 to 2.5, IV. SMB chromatography unit with an anion or cation exchanger resin.

FIG. 1 shows the feed stream (1) which is introduced into the Simulated Moving Bed chromatography (2), called SMB hereinafter. This is followed by a nanofiltration (4), which is connected by a connector (3) to the SMB. From there, the stream passes through a connector (5) into an apparatus for ion exchange (6) and, through a further connector (7), into an activated carbon column (8). The stream flows subsequently through a connector (9) into a reverse osmosis apparatus (10). From there, the stream divides. One branch leads via a connector (11) to a cooling crystallization (12), and the other branch returns via a connector (13) back into the media preparation stage or into the batch for the fermenter (14), which is positioned upstream of the feed stream (1). After the cooling crystallization (12), the stream divides into the product starting stream (16), one branch via a connector (17) into a second crystallization (18), one branch via a connector (22) into the esterification or other utilization (23), and one branch which leads, via a connector ( ) back to the nanofiltration (4) or via a connector (24) to the ion exchange (6). From the second cooling crystallizer (18), the stream divides via a connector (20) into the product starting stream (16) and the wastewater stream (21). Both cooling crystallizers (12) and (18) are coupled to a heat exchange apparatus (15) and (19).

Figure 2:
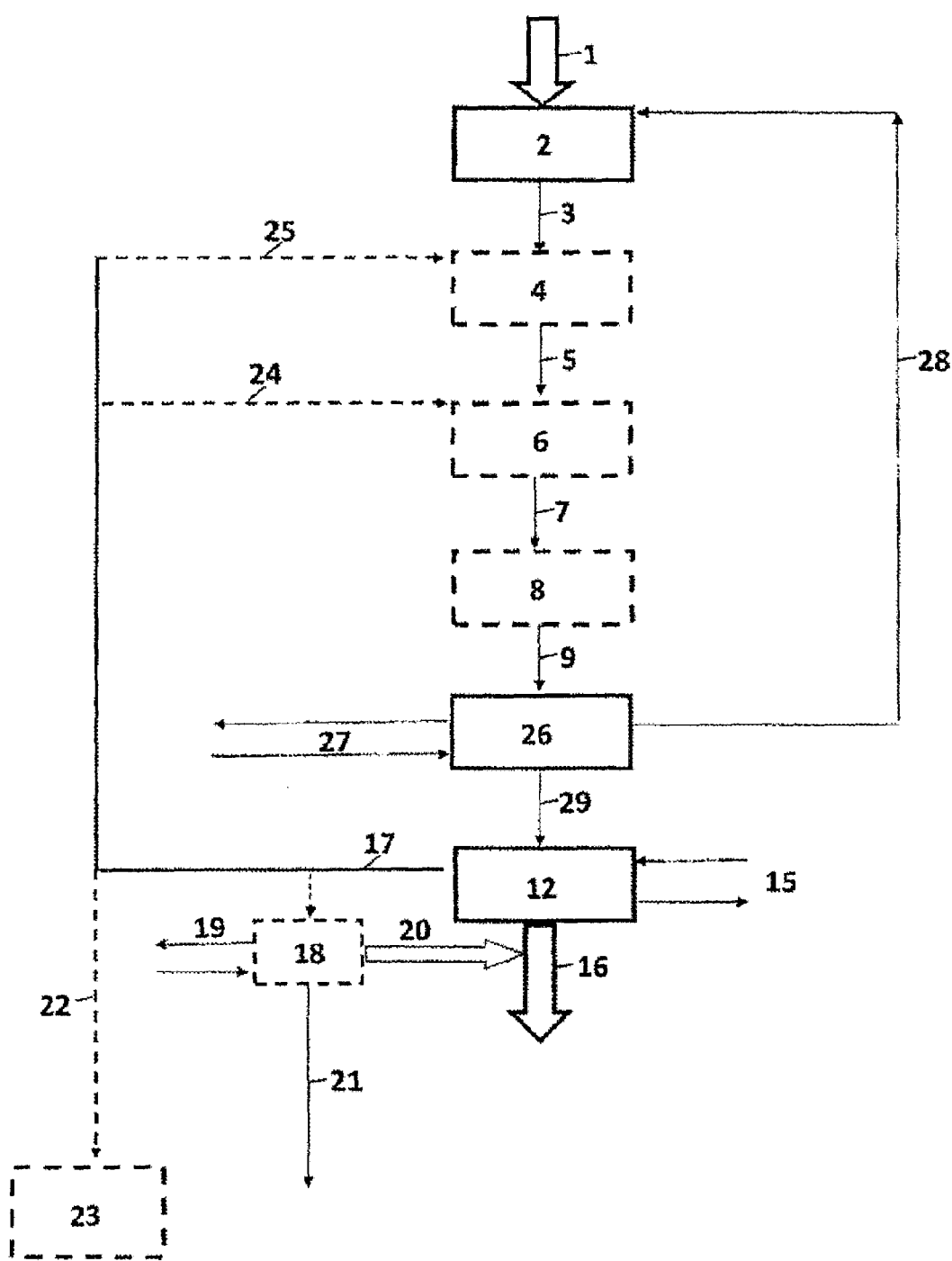
FIG. 2 is a flow diagram of an example method involving membrane distillation.

FIG. 2 shows the feed stream (1) which is introduced into the SMB (2). This is followed, via a connector (3), by a nanofiltration (4), by an apparatus for ion exchange (6) via a connector (5), and by an activated carbon column (8) via a further connector (7), followed by a connector (9), which leads to a membrane distillation (26), which is coupled to a cooling water circuit (27). From the membrane distillation (26), the stream divides. One branch leads via a connector (29) to a cooling crystallization (12), and the other branch leads via a connector (28) back into the SMB (2). The cooling crystallizer (12) is coupled to a further cooling water circuit (15). After the cooling crystallization (12) the stream divides into the product starting stream (16), one branch via a connector (17) into a second cooling crystallization (18), one branch via a connector (22) into the esterification or other utilization (23), and one branch which leads via a connector (25) back to the nanofiltration (4) or via the connector (24) to the ion exchange (6). From the second cooling crystallizer (18), the stream branches via a connector (20) into the product starting stream (16) and the wastewater stream (21).

Figure 3:
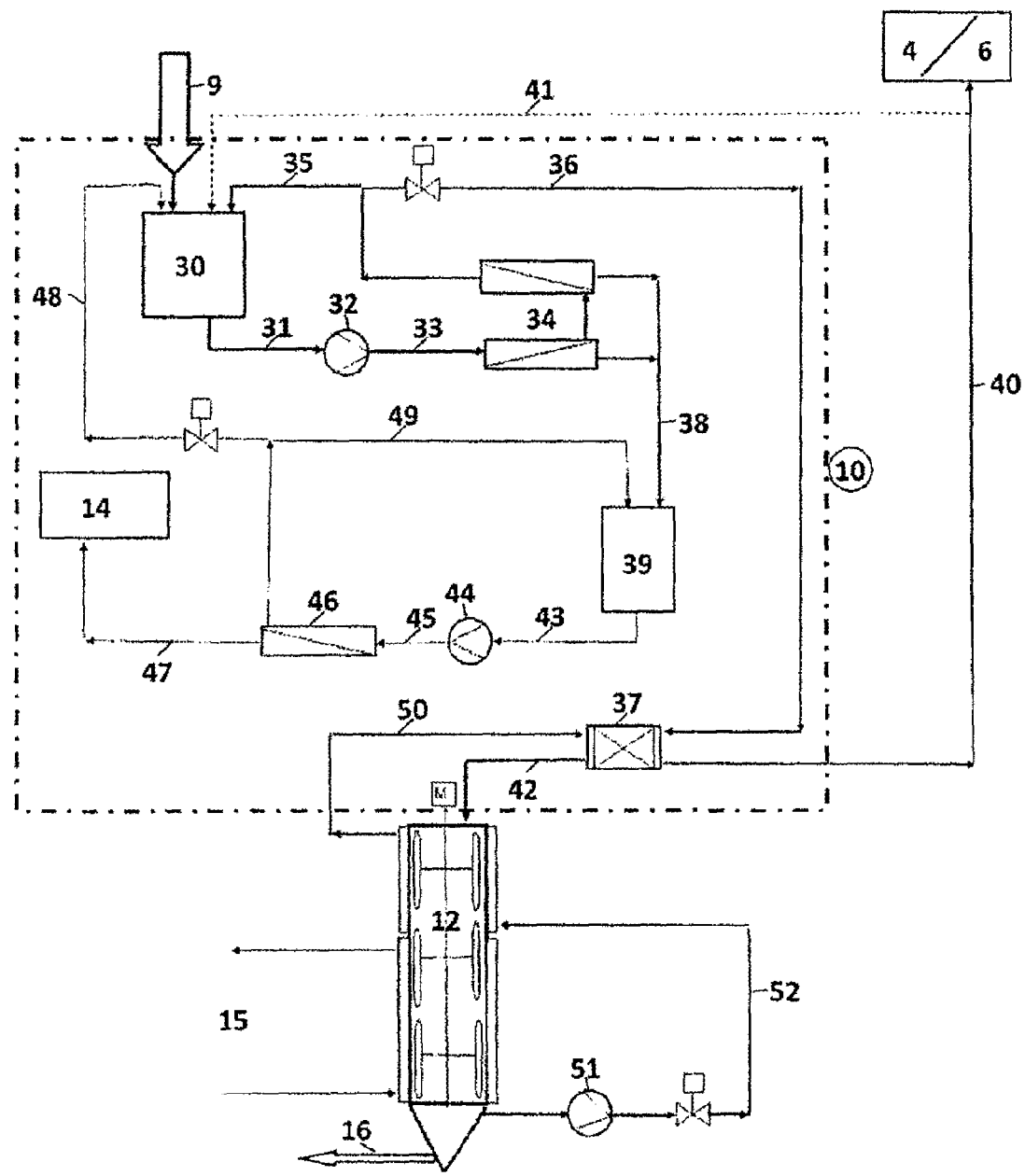
FIG. 3 is a flow diagram of an example method involving a combination of reverse osmosis and cooling crystallizer.

FIG. 3 shows the feedstream (9), which is introduced into a reverse osmosis apparatus (10) consisting of two reverse osmosis stages. First of all, the feedstream (9) passes into a circulation vessel of the first reverse osmosis stage (30). This is followed via a connector (31) by a pump system (32) of the first reverse osmosis stage, followed by a further connector (33) and by the first reverse osmosis stage (34). From the first reverse osmosis stage, the stream divides. One branch leads via a connector (35) back into the circulation vessel (30), another leads via a connector (36) into the plate heat exchanger (37), hereinafter called PHE, and a third stream leads via a connector (38) into the circulation vessel (39) of the second reverse osmosis stage. From the PHE (37), via a connector (40) a stream from the nanofiltration (4) and/or returned to the ion exchange (6), which are positioned upstream of the feedstream (9), or via a connector (41) to the circulation vessel (30). Another stream passes from the PHE (37) via a connector (42) to the cooling crystallizer (12). From the circulation vessel (39), the stream is guided via a connector (43) to a pump system (44) of the second reverse osmosis stage, before passing via a connector (45) into the second reverse osmosis stage (46). Downstream of the second reverse osmosis stage (46), the stream branches into one branch which leads, via a connector (47), back to the media preparation stage (14), and one branch which returns the stream either via a connector (48) to the circulation vessel (30) or via a connector (49) to the circulation vessel (39). At the cooling crystallizer (12), which is coupled with a cooling water circuit (15), the stream divides again. One stream is guided back from the upper part of the cooling crystallizer via a connector (50) into the PHE (37); another stream passes through the cooling crystallizer (12) and is pumped by a take-off pump (51) via a connector (52) back into the upper part of the cooling crystallizer (12); and a final stream corresponds to the product starting stream (16).

EXAMPLE

In the experiments, an aqueous succinic acid process solution having a succinic acid content of 40 g/l was supplied at a temperature of 40° C. to a reverse osmosis system and was concentrated under pressures of 40 to 60 bar. The specific permeate flow was adjusted by a pressure regulator to levels of between 10 and 30 l/m²h.

Concentration was carried out up to a succinic acid concentration of approximately 150 g/l. The concentrate thus obtained was then cooled to a temperature of 25° C., allowing approximately 70 g/l of succinic acid to be crystallized out. The mother liquor from the cooling crystallization, following removal of the crystals, was reheated to 40° C. and, by reverse osmosis, concentrated again up to a concentration of approximately 150 g/l.

In the experiments, overall, a volumetric concentration of 85% to 90% was achieved. Permeate flows of approximately 10 l/m²h were achieved here under pressures of up to 60 bar maximum.

Essentially only electrical energy is needed, since the thermal energy for heating the solution can largely be recovered by heat exchangers from the solution to be cooled. In particular, however, no thermal energy is needed for evaporative concentration.

In the context of the application of the invention, the membrane selection must be made on the one hand such that the component intended for crystallization is retained to a sufficient extent, and on the other hand the membrane must have sufficient permeability in order to ensure a sufficient permeate flow at the high osmotic pressure of the component in question.

Other dissolved components which give rise to osmotic pressure are removed in accordance with the invention by means of pretreatment (nanofiltration, ion exchange).

The operation of the membrane stage must be such that there is no possibility of crystals forming within the membrane elements, even in dead flow zones and even when concentration polarization is high and viscosity of the mother liquor is high, since otherwise the membrane element blocks. In accordance with the invention, this is achieved by raising the temperature of the mother liquor at intervals by approximately 4 K to 5 K, with the pressure reduced simultaneously, and therefore redissolving any crystals present which have formed, without employing purification means.

A further advantage (especially for temperature-sensitive substances) of the membrane cooling crystallization is the fact that it can be carried out, without extra cost and complexity, at a much lower temperature (approximately 40° C.) than an evaporative crystallization (at least 80° C.).

In order to increase product purity, unwanted components which also crystallize out and/or which disrupt crystallization can be removed from the mother liquor prior to the crystallization.

In the membrane cooling crystallization of succinic acid with a content of 40 g/kg, first of all a volumetric concentration by a factor of 2.3 was established in the experiments, corresponding to a yield of 56%. After cooling crystallization at 25° C., the mother liquor obtained was returned to the membrane stage and concentrated again by a factor of 2. With a three-stage regime of this kind, the residual quantity of mother liquor is approximately 10%, and in the case of a four-stage regime only 5%, of the original volume.

In the event of overpressure occurring, after each stage, the system is let down to atmospheric pressure prior to the crystallization.

In order to reduce the electrical energy demand, two procedures can be employed:
  crystallization under pressure, using a hydrocyclone, for example
  energy recovery from the concentrate during letdown By utilizing a combination of a concentration by reverse osmosis at a temperature of 40° C. and subsequent cooling to room temperature, it was possible to obtain succinic acid with a remaining acetic acid content of only 70 ppm, the acetic acid content being at a level of <1 ppm after a single recrystallization.

The advantages of the invention are that essentially only electrical energy is required. The thermal energy required for heating the solution is largely recovered by heat exchangers from the solution to be cooled. The energy expenditure for the method of purification and crystallization of organic acids is therefore significantly reduced. Here, furthermore, in contrast to existing methods, a cooling crystallization is used rather than an evaporative crystallization. In this way, no thermal energy is needed to concentrate the organic acid solutions by evaporation, thus denoting a considerable reduction in the energy expenditure, since the evaporative crystallization of a solution of succinic acid with a content of 40 g/kg solution, even in a multistage evaporator with heat recovery, requires a thermal energy of 20 MJ/kg succinic acid.

The use of a membrane cooling crystallization is appropriate in particular for temperature-sensitive substances. It can be carried out without extra expenditure at a significantly lower temperature of approximately 40° C., whereas an evaporative crystallization takes place at temperatures of at least 80° C.

Furthermore, the electrical energy requirement can be reduced further by carrying out the crystallization under pressure, using a hydrocyclone, for example, and recovering energy from the concentrate on letdown.

A further advantage of the invention is that, since the mother liquor drawn off from the crystallizer is reheated and then returned to the feed reservoir for the reverse osmosis, and therefore enters the crystallizer more than once, the residual quantity of mother liquor is only around 10% of the original volume. In this way, almost all of the acid solution is converted into crystals of organic acids.

Furthermore, by using the cooling crystallization, the process steps of polishing can be reduced. It would therefore be possible to do without the activated carbon column, with the polishing process therefore consisting solely of a nanofiltration in combination with an ion exchange, while nevertheless allowing crystals of high purity (≥99%) to be obtained.

REFERENCE NUMERALS

1 Feed stream
2 Simulated Moving Bed chromatography (SMB)
3 Connector
4 Nanofiltration
5 Connector
6 Ion exchange
7 Connector
8 Activated carbon column
9 Connector
10 Reverse osmosis
11 Connector
12 Cooling crystallization
13 Connector
14 Media preparation, fermenter batch
15 Cooling water circuit
16 Product starting stream
17 Connecting stream
18 Second cooling crystallizer
19 Cooling brine
20 Product starting stream
21 Wastewater stream
22 Connector
23 Esterification or other utilization
24 Connector
25 Connector
26 Membrane distillation
27 Cooling water circuit
28 Recycle stream
29 Connector
30 Circulation vessel of the first reverse osmosis stage
31 Connector
32 Pump system of the first reverse osmosis stage
33 Connector
34 First reverse osmosis stage
35 Connector
36 Connector
37 Plate heat exchanger (PHE)
38 Connector
39 Circulation vessel of the second reverse osmosis stage
40 Connector
41 Connector
42 Connector
43 Connector
44 Pump system of the second reverse osmosis stage
45 Connector
46 Second reverse osmosis stage
47 Connector
48 Connector
49 Connector
50 Connector
51 Take-off pump
52 Connector

What is claimed is:

1. A method for concentrating and crystallizing fermentable carboxylic acids, salts, and mixtures thereof, the method comprising:
   providing a processed fermentation broth or an aqueous solution of a carboxylic acid,
      wherein the carboxylic acid has a molar mass in a range from 90 to 210 g/mol,
      wherein the carboxylic acid has a solubility in water at 20° C. of 4 g/l to 100 g/l,
      wherein the carboxylic acid has a relative increase in solubility in a temperature range from 20 to 80° C. of at least 2%/° C. relative to the solubility at 20° C., and
      wherein a concentrated solution of the carboxylic acid has an osmotic pressure in a temperature range from 20 to 80° C. of less than 80 bar;
   concentrating the carboxylic acid in the processed fermentation broth or the aqueous solution by way of a membrane method, wherein the carboxylic acid is concentrated in the processed fermentation broth or the aqueous solution by a factor of 1 to 5 up to immediately before attainment of a solubility limit of the carboxylic acid;
   subjecting the concentrated processed fermentation broth or the aqueous solution of the carboxylic acid to a cooling crystallization; and
   isolating crystals of the carboxylic acid.

2. The method of claim 1 comprising concentrating the carboxylic acid in the processed fermentation broth or the aqueous solution such that a concentration of the carboxylic acid in the processed fermentation broth or the aqueous solution increases from 1 to 10% by weight to 12 to 25% by weight.

3. The method of claim 1 comprising concentrating the carboxylic acid in the processed fermentation broth or the aqueous solution to a degree such that supersaturation of the processed fermentation broth or the aqueous solution and therewith incipient crystallization occur on cooling to 10 to 40° C.

4. The method of claim 1 wherein the membrane method comprises at least one of nanofiltration, reverse osmosis, or membrane distillation for separation into a concentrate and a permeate, wherein the nanofiltration, the reverse osmosis, and the membrane distillation can be performed in one-stage form, in two-stage form, in multistage form, or in combination with one another.

5. The method of claim 4 comprising performing the reverse osmosis in two-stage form, with a permeate of a first reverse osmosis stage being supplied to a second reverse osmosis stage, with a permeate of the second reverse osmosis stage being used to prepare a nutrient solution for fermentation.

6. The method of claim 1 wherein the concentrating occurs by way of membrane distillation and a distillate of the membrane distillation is used as an eluent for a subsequent chromatographic purification step, wherein the membrane distillation is performed at temperatures below a solubility limit of the carboxylic acid.

7. The method of claim 1 further comprising subjecting a concentrate from the membrane method to regenerative heat exchange in a heat exchanger, wherein the regenerative heat exchange occurs with a mother liquor drawn off from the cooling crystallization, wherein the concentrate is cooled to a temperature of 30 to 40° C. and then supplied to the cooling crystallization.

8. The method of claim 7 further comprising returning the mother liquor heated in the heat exchanger to the processed fermentation broth or the aqueous solution, wherein the mother liquor is purified by at least one of nanofiltration or ion exchange before being returned to the processed fermentation broth or the aqueous solution.

9. The method of claim 7 wherein in the cooling crystallization, the crystals are precipitated in the mother liquor, wherein the mother liquor that is separated from the crystals is returned for further use in the method.

10. The method of claim 9 wherein the cooling crystallization is carried out in two-stage form, with a first stage of the cooling crystallization comprising cooling with the mother liquor drawn off from a cooling crystallizer, with a second stage of the cooling crystallization comprising cooling with externally supplied cooling water or cooling brine.

11. The method of claim 1 wherein the cooling crystallization is performed in a contact crystallizer.

12. The method of claim 1 wherein steps for processing the fermentation broth comprise:
  removing biomass from the fermentation broth by a first step of at least one of centrifugation, separation, precoat filtration, or microfiltration and a second step of ultrafiltration;
  acidifying the fermentation broth with sulfuric acid, which results in a solution; and
  performing SMB chromatography with the solution.

13. The method of claim 1 wherein the carboxylic acid has at least one of a molar mass of 110 g/mol to 150 g/mol or a solubility in water at 20° C. of 15 g/l to 90 g/l.

14. The method of claim 1 wherein the carboxylic acid is selected from a group consisting of fumaric acid, succinic acid, adipic acid, itaconic acid, threonine, methionine, aspartic acid, glutaric acid, asparagine, glutamine, histidine, isoleucine, phenylalanine, tryptophan, tyrosine, valine, salts thereof, and mixtures thereof.

15. An apparatus for concentrating and crystallizing fermentable carboxylic acids, salts, and mixtures thereof, the apparatus comprising:
  at least one of a nanofiltration unit, a reverse osmosis unit, or a membrane distillation unit for separating a processed fermentation broth originating from a fermenter into a concentrate stream and a permeate stream, wherein the at least one of the nanofiltration unit, the reverse osmosis unit, or the membrane distillation unit comprises a diverting line for recycling the permeate stream; and
  a cooling crystallization unit that is single-stage or multistage for crystallizing the carboxylic acid out of a solution, wherein the cooling crystallization unit comprises a recycle line for a mother liquor as coolant for the cooling crystallization unit,
  wherein the at least one of the nanofiltration unit, the reverse osmosis unit, or the membrane distillation unit is connected to the cooling crystallization unit via a line for transferring the concentrate stream into the cooling crystallization unit.

16. The apparatus of claim 15 wherein the at least one of the nanofiltration unit, the reverse osmosis unit, or the membrane distillation unit comprises a two-stage reverse osmosis unit with a first stage being connected to a second stage via permeate stream line for transferring the permeate stream from the first stage to the second stage.

17. The apparatus of claim 15 wherein the cooling crystallization unit comprises a two-stage cooling crystallization unit with separate coolant systems, wherein a first stage of the cooling crystallization unit is connected to a second stage of the cooling crystallization unit via a recycle line for the mother liquor with a coolant system of the first stage, wherein a coolant system of the second stage has a separate feed line for a coolant.

18. The apparatus of claim 15 wherein the line for transferring the concentrate stream into the cooling crystallization unit is interrupted by a heat exchanger comprising:
  for the concentrate stream, a feed line from the at least one of the nanofiltration unit, the reverse osmosis unit, or the membrane distillation unit and a diverting line to the cooling crystallization unit; and
  for the mother liquor, a feed line from the cooling crystallization unit and a diverting line to the processed fermentation broth,
  which thereby enable regenerative heat exchange between the concentrate stream and a mother liquor stream.

19. The apparatus of claim 15 wherein the cooling crystallization unit is a contact crystallizer.

20. The apparatus of claim 15 wherein for processing the fermentation broth the apparatus further comprises:
  a removal unit for removing the biomass from the fermentation broth, wherein the removal unit comprises at least one of a centrifuge, a separator, a precoat filtration unit, a microfiltration unit, or a ultrafiltration unit;
  a reactor for acidifying the fermentation broth with sulfuric acid; and
  a SMB chromatography unit with an anion or cation exchanger resin.

21. A method for concentrating and crystallizing fermentable carboxylic acids, salts, and mixtures thereof, the method comprising:
  providing a processed fermentation broth or an aqueous solution of a carboxylic acid,
  wherein the carboxylic acid has a molar mass in a range from 90 to 210 g/mol,
  wherein the carboxylic acid has a solubility in water at 20° C. of 4 g/l to 100 g/l,
  wherein the carboxylic acid has a relative increase in solubility in a temperature range from 20 to 80° C. of at least 2%/° C. relative to the solubility at 20° C., and wherein a concentrated solution of the carboxylic acid has an osmotic pressure in a temperature range from 20 to 80° C. of less than 80 bar;

concentrating the carboxylic acid in the processed fermentation broth or the aqueous solution by way of a membrane method, wherein the concentrating occurs by way of membrane distillation and a distillate of the membrane distillation is used as an eluent for a subsequent chromatographic purification step, wherein the membrane distillation is performed at temperatures below a solubility limit of the carboxylic acid;

subjecting the concentrated processed fermentation broth or the aqueous solution of the carboxylic acid to a cooling crystallization; and isolating crystals of the carboxylic acid.

* * * * *